(12) United States Patent
Lee et al.

(10) Patent No.: US 9,394,242 B2
(45) Date of Patent: Jul. 19, 2016

(54) METHOD FOR PREPARING DINITRILE COMPOUND

(71) Applicant: LG CHEM, LTD., Seoul (KR)

(72) Inventors: Byoung-Bae Lee, Daejeon (KR); Jae-Seung Oh, Seoul (KR); You-Jin Shim, Daejeon (KR); Yeon-Suk Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/026,233

(22) Filed: Sep. 13, 2013

(65) Prior Publication Data

US 2014/0018567 A1 Jan. 16, 2014

Related U.S. Application Data

(63) Continuation of application No. PCT/KR2012/000485, filed on Jan. 19, 2012.

(30) Foreign Application Priority Data

Mar. 18, 2011 (KR) .................. 10-2011-0024437
Jan. 12, 2012 (KR) .................. 10-2012-0003863

(51) Int. Cl.
*C07C 253/30* (2006.01)
*B01J 31/02* (2006.01)
*C07C 255/13* (2006.01)

(52) U.S. Cl.
CPC ........... *C07C 253/30* (2013.01); *B01J 31/0212* (2013.01); *C07C 255/13* (2013.01); *B01J 2231/32* (2013.01)

(58) Field of Classification Search
CPC ...... C07C 253/30; C07C 31/20; C07C 41/06; C07C 255/13
USPC .......................................... 558/450
See application file for complete search history.

(56) References Cited

U.S. PATENT DOCUMENTS 2,941,990 A * 6/1960 Schuller ................ C08F 257/02
525/242
2,977,337 A * 3/1961 Schuller .................... C08F 8/30
525/242

FOREIGN PATENT DOCUMENTS

| CA | 1119193 A | * | 3/1982 |
| JP | 2005-263716 A | | 9/2005 |
| JP | 2005-263717 A | | 9/2005 |
| WO | WO 2009/152392 A2 | | 12/2009 |

OTHER PUBLICATIONS

Yamaguchi et al. "Method for producing cyanoalkoxy compound." JP2005-263717A, English Machine Translation obtained Sep. 24, 2014.*
Partial Translation of JP2005-263717A [0020-0023], Irina Knizhnik, USPTO, Alexandria, VA (Apr. 2015).*
Yamaguchi et al. JP2005-263717A (Sep. 29, 2005) Replacement: English Machine Translation.*
Bruson, H. A. "Cyanoethylation" Org. React. 2011, 5(2), 79-135 (Mar. 15, 2011).*
International Search Report issued in PCT/KR2012/000485 mailed Aug. 14, 2012.

* cited by examiner

*Primary Examiner* — Nyeemah A Grazier
*Assistant Examiner* — Amanda L Aguirre
(74) *Attorney, Agent, or Firm* — Birch, Stewart, Kolasch & Birch, LLP

(57) ABSTRACT

Disclosed is a method for preparing a dinitrile compound. The method includes reacting an alcohol compound with a nitrile compound having a terminal carbon-carbon unsaturated bond under anhydrous conditions. A potassium alkoxide having 1 to 5 carbon atoms is used as a catalyst in the course of the reaction. According to the method, a high-purity dinitrile compound can be prepared in a simple manner within a short reaction time indicating high productivity.

7 Claims, 2 Drawing Sheets

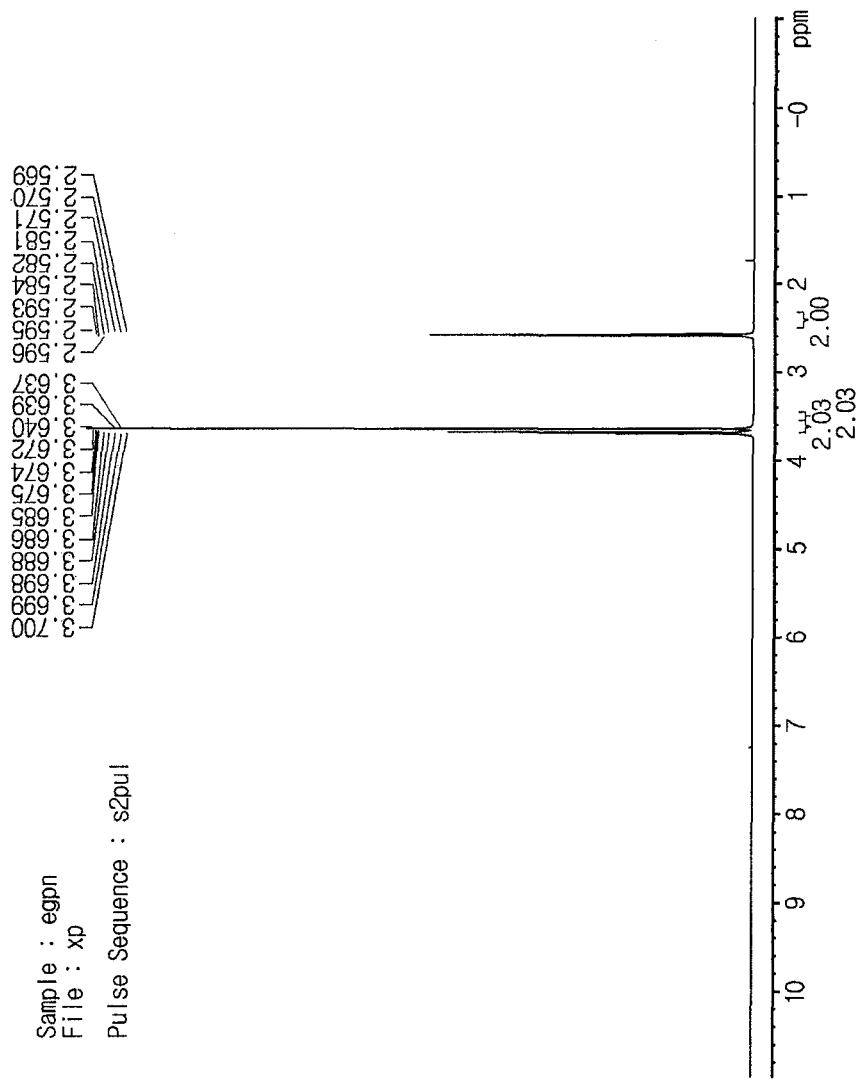
FIG. 1 (Example 1)

FIG. 2 (Example 1)
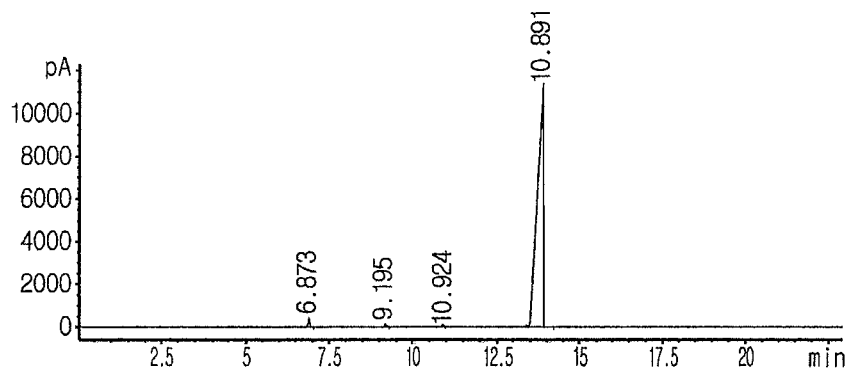
FIG. 3 (Comparative Example 1)
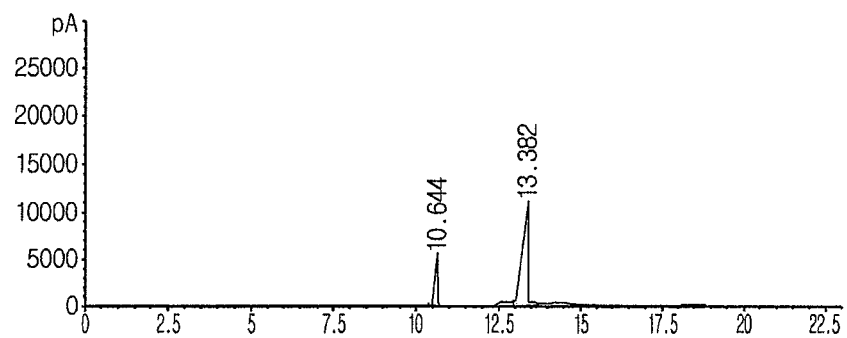

METHOD FOR PREPARING DINITRILE COMPOUND

CROSS-REFERENCE TO RELATED APPLICATION

This application is a continuation of International Application No. PCT/KR2012/000485 filed on Jan. 19, 2012, which claims priority to Korean Patent Application Nos. 10-2011-0024437 and 10-2012-0003863 filed in the Republic of Korea on Mar. 18, 2011 and Jan. 12, 2012, respectively, the entire contents of which are incorporated herein by reference.

TECHNICAL FIELD

The present disclosure relates to a method for preparing a dinitrile compound, and more specifically to a method for preparing a dinitrile compound in a simple manner without accompanying the formation of any impurity.

BACKGROUND ART

Energy storage technologies have received more and more attention in recent years. As the applicability of energy storage technology is extended to mobile phones, camcorders, notebook PCs and even electric automobiles, there is a growing demand for high energy-density batteries as power sources for such electronic devices. As batteries capable of meeting this demand, lithium secondary batteries are considered the most promising batteries and are being actively researched.

Many secondary batteries are currently available. Of these, a typical example of the lithium secondary batteries developed in the early 1990's includes an anode made of a carbonaceous material capable of intercalating/deintercalating lithium ions, a cathode made of a lithium-containing oxide, and a non-aqueous electrolyte solution containing an appropriate amount of a lithium salt in a mixed organic solvent.

Non-aqueous electrolyte solutions containing organic solvents are prone to oxidation during long-term storage at high temperatures. This oxidation causes gas evolution and thus leads to the swelling of batteries, eventually resulting in degradation of the batteries. The gases arising from the decomposition of the electrolyte solutions may deform pouch or can type battery assemblies to cause internal short circuits. In extreme cases, the batteries may catch fire or explode. The oxidation of the electrolyte solutions may be accelerated by transition metals dissolved out under high voltage conditions.

In efforts to solve such problems, various additives have been proposed to prevent the swelling of batteries in non-aqueous electrolyte solutions. An example of such additives is a dinitrile compound having two or more ether bonds. The dinitrile compound is known to inhibit oxidation between an electrolyte solution and a cathode to suppress heat release. The dinitrile compound is also known to inhibit oxidative decomposition of an electrolyte solution to prevent a battery from swelling.

In a general method for the preparation of the dinitrile compound, a base catalyst, such as an alkali metal hydroxide or a quaternary ammonium compound, is used for a cyanoethylation reaction between an alcohol compound and acrylonitrile. The use of sodium hydroxide, which is most economically advantageous and is easy to synthesize, is widely known as the base catalyst.

However, water used as a mediator for the cyanoethylation reaction reacts with acrylonitrile to form cyanoethanol, which further reacts with acrylonitrile to form bis(2-cyanoethyl)ether, which acts as an impurity.

Some methods have been attempted to suppress the formation of the by-product, for example, by controlling the amount of acrylonitrile consumed in the reaction and by dropping acrylonitrile at a low rate to control the acrylonitrile concentration. However, these methods suffer from some problems, such as an increase in the amount of the alcohol compound remaining in the reaction mixture, causing low quality of the final product.

Another possible method is to prevent the occurrence of cyanoethylation due to the presence of water by reacting the reactants under non-aqueous conditions. In this case, however, the polymerization of acrylonitrile may occur depending on the presence of an alkali metal hydroxide or an organic base, leading to discoloration of the reactants.

On the other hand, a suggestion to solve such problems is described in Japanese Patent Registration No. 3946825, which discloses a method for preparing a cyanoethyl compound in the presence of lithium hydroxide as a reaction catalyst under anhydrous conditions. This method was reported to be useful in suppressing the formation of bis(2-cyanoethyl)ether and reducing the occurrence of coloring due to the polymerization of acrylonitrile.

However, lithium hydroxide is not effective in preventing the polymerization of the nitrile compound having an unsaturated bond and its relatively low solubility increases the reaction time.

DISCLOSURE

Technical Problem

The present disclosure is designed to solve the problems of the prior art, and therefore it is an object of the present disclosure to provide a method for preparing a high-purity dinitrile compound in a simple manner within a short reaction time indicating high productivity.

Technical Solution

According to the present disclosure, there is provided a method for preparing a dinitrile compound, the method including reacting an alcohol compound with a nitrile compound having a terminal carbon-carbon unsaturated bond under anhydrous conditions wherein a potassium alkoxide having 1 to 5 carbon atoms is used as a catalyst for the reaction.

Any compound in which a $C_1$-$C_5$ alkoxy group is bonded to potassium (K) may be used without particular limitation as the potassium alkoxide. Examples of potassium alkoxides suitable for use in the method of the present disclosure include, but are not limited to, potassium methoxide, potassium ethoxide, potassium tert-butoxide and potassium tert-pentoxide. These potassium alkoxides may be used alone or as a mixture of two or more thereof.

The content of the potassium alkoxide may vary depending on the specific kind of intended dinitrile compound, etc. For example, the potassium alkoxide may be used in an amount of 0.01 to 5 parts by weight, based on 100 parts by weight of the alcohol compound, but is not limited to this range.

The alcohol compound used for the preparation of a dinitrile compound in the method of the present disclosure may be a polyhydric alcohol. The alcohol compound is preferably a dihydric alcohol. More specific examples of alcohol compounds suitable for use in the method of the present disclosure include ethylene glycol, propylene glycol, butylene glycol and pentylene glycol. These alcohol compounds may be used alone or as a mixture of two or more thereof.

Examples of nitrile compounds having a terminal carbon-carbon unsaturated bond suitable for use in the preparation of a dinitrile compound include acrylonitrile, 3-butenenitrile and 4-pentenenitrile. These nitrile compounds may be used alone or as a mixture of two or more thereof.

The reaction may be carried out at a relatively low temperature of 20 to 50° C.

Advantageous Effects

According to the method of the present disclosure, the reaction is carried out under anhydrous conditions so that the formation of bis(2-cyanoethyl)ether as a by-product can be suppressed and the polymerization of the nitrile compound having a carbon-carbon unsaturated bond can be inhibited to prevent the occurrence of coloring. In addition, the reaction time is short, contributing to a marked improvement in productivity.

DESCRIPTION OF DRAWINGS

The accompanying drawings illustrate preferred embodiments of the present disclosure and, together with the foregoing disclosure, serve to provide further understanding of the technical spirit of the present disclosure. However, the present disclosure is not to be construed as being limited to the drawings.

FIG. 1 is a nuclear magnetic resonance (NMR) spectrum of a dinitrile compound prepared in Example 1.

FIG. 2 is a gas chromatograph of a dinitrile compound prepared in Example 1.

FIG. 3 is a gas chromatograph of a dinitrile compound prepared in Comparative Example 1.

MODE FOR DISCLOSURE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

The present disclosure provides a method for preparing a dinitrile compound. The method of the present disclosure is characterized by the reaction of an alcohol compound with a nitrile compound having a terminal carbon-carbon unsaturated bond under anhydrous conditions and the use of a potassium alkoxide having 1 to 5 carbon atoms as a catalyst in the course of the reaction.

Alkali metal hydroxides and organic bases have been used as catalysts for the preparation of dinitrile compounds. However, these catalysts polymerize nitrile compounds having an unsaturated bond, causing discoloration of reactants.

In contrast, the use of the potassium alkoxide as a catalyst in the method of the present disclosure does not cause the polymerization of the nitrile compound having an unsaturated bond, avoiding the discoloration of the reactants. Furthermore, high solubility of the potassium alkoxide shortens the time required for dissolution, leading to high productivity.

In addition, the reaction under anhydrous conditions in the presence of the potassium alkoxide enables the preparation of a dinitrile compound in high purity without accompanying the formation of any impurity.

There is no particular restriction on the kind of the potassium alkoxide. For example, the potassium alkoxide may be any compound in which a $C_1$-$C_5$ alkoxy group is bonded to potassium (K). Examples of potassium alkoxides suitable for use in the method of the present disclosure include, but are not limited to, potassium methoxide, potassium ethoxide, potassium tert-butoxide and potassium tert-pentoxide. These potassium alkoxides may be used alone or as a mixture of two or more thereof.

The amount of the potassium alkoxide used for the reaction may be suitably chosen depending on the specific kind of an intended dinitrile compound and the kinds and contents of the alcohol compound and the nitrile compound having an unsaturated bond as reactants. For example, the potassium alkoxide may be used in an amount of 0.01 to 5 parts by weight, based on 100 parts by weight of the alcohol compound, but is not limited to this range. If the amount of the potassium alkoxide is less than 0.01 parts by weight, the reaction rate may be slow. Meanwhile, if the amount of the potassium alkoxide exceeds 5 parts by weight, it will no longer exhibit the desired effect of using the catalyst, i.e. increase in reactivity, and it may not be easy to remove the catalyst after completion of the reaction.

The alcohol compound used as a reactant in the method of the present disclosure is one having one or more alcohol groups (—OH). The alcohol compound is not particularly limited so long as it can be used for the preparation of a dinitrile compound. The number of carbon atoms in the alcohol compound is, for example, from 1 to 10, preferably from 1 to 5, more preferably from 2 to 5, but is not limited thereto. The alcohol compound is preferably a dihydric alcohol.

Specific examples of alcohol compounds suitable for use in the method of the present disclosure include, but are not limited to, ethylene glycol, propylene glycol, butylene glycol and pentylene glycol. These alcohol compounds may be used alone or as a mixture of two or more thereof.

The nitrile compound having a terminal carbon-carbon unsaturated bond as another reactant used in the method of the present disclosure is one that has a nitrile group at one end of the molecule and a carbon-carbon unsaturated bond at the other end. For example, the nitrile compound may be a compound in which a nitrile group is bonded to a carbon-carbon unsaturated bond through at least one alkylene group. Specific examples of nitrile compounds having an unsaturated bond suitable for use in the method of the present disclosure include, but are not limited to, acrylonitrile, 3-butenenitrile and 4-pentenenitrile. These nitrile compounds may be used alone or as a mixture of two or more thereof.

According to the method of the present disclosure, a dinitrile compound can be prepared using the reactants and the catalyst in a simple way. An embodiment of the method will be described in more detail below.

The potassium alkoxide catalyst is added to and sufficiently mixed with the alcohol compound under heating and/or with stirring until its complete dissolution. Thereafter, the unsaturated nitrile compound is slowly added dropwise to initiate the formation of a dinitrile compound. After the dropwise addition is finished, the reactants are sufficiently mixed by a suitable process, such as stirring, to complete the formation of the dinitrile compound. After completion of the reaction, the dinitrile compound is separated using a proper solvent, followed by filtration.

The method of the present disclosure can be carried out at a relatively low temperature, for example, from 20 to 50° C., enabling the preparation of a dinitrile compound in a simple and easy manner.

Those skilled in the art can appropriately determine the mixing ratio between the alcohol compound and the nitrile compound having an unsaturated bond taking into consideration the specific kind of an intended dinitrile compound.

The present disclosure also provides a dinitrile compound prepared by the method. The dinitrile compound of the present disclosure is preferably one that has two or more ether bonds. Specifically, the dinitrile compound of the present disclosure may be represented by Formula 1:

$$NC-R^1+O-R^2+O-R^3-CN \quad (1)$$

wherein $R^1$, $R^2$ and $R^3$ are each independently $C_1$-$C_5$ alkylene or alkenylene and m is an integer from 1 to 5.

More specifically, the dinitrile compound of the present disclosure can be selected from the group consisting of, but not limited to, 3,5-dioxa-heptanedinitrile, 1,4-bis(cyanoethoxy)butane, bis(2-cyanoethyl)-monoformal, bis(2-cyanoethyl)-diformal, bis(2-cyanoethyl)-triformal, ethylene glycol bis(2-cyanoethyl)ether, bis(2-(2-cyanoethoxy)ethyl)ether, 4,7,10,13-tetraoxahexadecanedinitrile, 4,7,10,13,16-pentaoxanonadecane-1,14-dinitrile, 3,6,9,12,15,18-hexaoxaeicosan dinitrile, 4,10-dioxa-undecanedinitrile, 1,10-dicyano-3,8-dioxadecane, 4,10-dioxa-tridecanedinitrile and 6,9-dioxa-tetradecanedinitrile.

The present disclosure also provides a non-aqueous electrolyte solution for a lithium secondary battery wherein the non-aqueous electrolyte solution includes a lithium salt, an organic solvent and the dinitrile compound as an additive.

The dinitrile compound having ether bonds according to the present disclosure can form a complex on the surface of a cathode composed of a lithium-transition metal oxide. This complexation inhibits oxidation between the electrolyte solution and the cathode to suppress heat release and prevents a steep rise in the temperature of a battery to protect the battery from internal short circuits.

Various kinds of compounds exist in non-aqueous electrolyte solutions during charge and discharge. Particularly, such compounds as HF and $PF_5$ make the atmosphere of non-aqueous electrolyte solutions acidic. This acidic atmosphere accelerates the oxidation of non-aqueous electrolyte solutions on the surface of cathodes. The oxygen atoms (—O—) present in the dinitrile compound having ether bonds according to the present disclosure bond to such compounds as HF and $PF_5$ in non-aqueous electrolyte solutions to suppress the creation of an acidic atmosphere, which can also protect the non-aqueous electrolyte solutions from oxidative degradation.

The dinitrile compound having ether bonds according to the present disclosure can exhibit improved effects in terms of battery performance compared to other known additives. Specifically, the use of the dinitrile compound according to the present disclosure can impart a battery with excellent electrochemical properties, such as high capacity retention and improved charging and discharging cycle life.

The lithium salt as an electrolyte included in the non-aqueous electrolyte solution of the present disclosure may be any of those commonly used in electrolyte solutions for lithium secondary batteries. For example, the anion of the lithium salt may be selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ and $(CF_3CF_2SO_2)_2N^-$.

The organic solvent included in the non-aqueous electrolyte solution of the present disclosure may be any of those commonly used in electrolyte solutions for lithium secondary batteries. Non-limiting examples of organic solvents suitable for use in the non-aqueous electrolyte solution include, but are not limited to, ethers, esters, amides, linear carbonates and cyclic carbonates. These organic solvents may be used alone or as a mixture of two or more thereof.

The non-aqueous electrolyte solution may include a carbonate compound, such as a cyclic carbonate, a linear carbonate or a mixture thereof, as a representative example of the organic solvent. Specifically, the cyclic carbonate compound may be selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, halides thereof, and mixtures thereof. The linear carbonate compound may be selected from the group consisting of, but not limited to, dimethyl carbonate (DMC), diethyl carbonate (DEC), dipropyl carbonate, ethyl methyl carbonate (EMC), methyl propyl carbonate, ethyl propyl carbonate, and mixtures thereof.

Ethylene carbonate and propylene carbonate, which are highly viscous and high dielectric constant cyclic carbonates, are particularly preferred because of their good ability to dissociate the lithium salt present in the electrolyte solution. A mixture of such a cyclic carbonate and a linear carbonate whose viscosity and dielectric constant are low, such as dimethyl carbonate or diethyl carbonate, in a suitable ratio is more preferably used because it can be used to prepare an electrolyte solution having a high electrical conductivity.

Examples of the ethers include, but are not limited to, dimethyl ether, diethyl ether, dipropyl ether, methyl ethyl ether, methyl propyl ether and ethyl propyl ether. These ethers may be used alone or as a mixture of two or more thereof.

Examples of the esters include, but are not limited to, methyl acetate, ethyl acetate, propyl acetate, methyl propionate, ethyl propionate, γ-butyrolactone, γ-valerolactone, γ-caprolactone, σ-valerolactone and ϵ-caprolactone. These esters may be used alone or as a mixture of two or more thereof.

The non-aqueous electrolyte solution of the present disclosure can be injected into an electrode structure consisting of a cathode, an anode and a separator interposed between the electrodes to fabricate a lithium secondary battery. The cathode, the anode and the separator constituting the electrode structure may be those commonly used to fabricate lithium secondary batteries.

Hereinafter, embodiments of the present disclosure will be described in detail. The embodiments of the present disclosure, however, may take several other forms, and the scope of the present disclosure should not be construed as being limited to the following examples. The embodiments of the present disclosure are provided to more fully explain the present disclosure to those having ordinary knowledge in the art to which the present disclosure pertains.

EXAMPLE 1

124.2 g of ethylene glycol as an alcohol compound and 0.2 g of potassium tert-butoxide were placed in a flask and were stirred under heating at 40° C. To the mixture was added dropwise 222.8 g of acrylonitrile over 1 hr.

After the dropwise addition was finished, stirring was continued for an additional 4 hr. The reaction mixture was extracted with 200 g of methylene chloride and 500 g of distilled water. The extraction procedure was repeated once more. The methylene chloride solution was separated and distilled under reduced pressure, affording colorless and transparent ethylene glycol bis(2-cyanoethyl)ether.

The structure of the product was confirmed by NMR. The NMR spectrum is shown in FIG. 1.

The purity of the product was confirmed by gas chromatography (GC). The results are shown is FIG. 2. The graph of FIG. 2 reveals that the product had a purity of 99% or higher.

COMPARATIVE EXAMPLE 1

124.2 g of ethylene glycol as an alcohol compound and a 2% aqueous solution of sodium hydroxide were placed in a flask and were stirred under heating at 40° C. To the mixture was added dropwise 222.8 g of acrylonitrile over 1 hr.

After the dropwise addition was finished, stirring was continued for an additional 3 hr. The reaction mixture was extracted with 200 g of methylene chloride and 500 g of distilled water. The extraction procedure was repeated once more. The methylene chloride solution was separated and distilled under reduced pressure, affording colorless and transparent ethylene glycol bis(2-cyanoethyl)ether.

The purity of the product was confirmed by gas chromatography (GC). The results are shown is FIG. 3. The graph of FIG. 3 reveals that the product had a purity of 79% and bis(2-cyanoethyl)ether as a by-product was formed in an amount of 21%.

From these results, can be confirmed that the aqueous conditions for the reaction in Comparative Example 1 led to the formation of the by-product, bis(2-cyanoethyl)ether, which is a cause of the lower purity, unlike the anhydrous conditions for the reaction in Example 1.

COMPARATIVE EXAMPLE 2

124.2 g of ethylene glycol as an alcohol compound and 0.1 g of sodium hydroxide were placed in a flask and were stirred under heating at 40-50° C. To the mixture was added dropwise 222.8 g of acrylonitrile over 2 hr.

The reaction mixture began to discolor from an hour after initiation of the dropwise addition and turned black along with precipitation after completion of the dropwise addition. After the reaction was finished, the formation of the desired product, ethylene glycol bis(2-cyanoethyl)ether, could not be confirmed by gas chromatography.

From these results, it can be seen that the polymerization of the acrylonitrile as a raw material impeded the formation of the desired product and caused the occurrence of coloring.

What is claimed is:

1. A method for preparing a dinitrile compound, the method comprising:

reacting an alcohol compound of the formula H—(O—$R^2$)$_m$—OH, wherein $R^2$ is $C_1$-$C_5$ alkylene or alkenylene and m is 1-5, with a nitrile compound having a terminal carbon-carbon unsaturated bond, where the nitrile group is bonded to the carbon-carbon unsaturated bond directly or through at least one alkylene, wherein the alcohol compound reacts with and adds to the terminal carbon of the carbon-carbon unsaturated bond of the nitrile compound, under anhydrous conditions, wherein a potassium alkoxide having 4 to 5 carbon atoms is used as a catalyst for the reaction, and wherein the reaction is carried by stirring the alcohol compound and the potassium alkoxide, adding the nitrile compound to prepare a reaction mixture, stirring the reaction mixture, wherein the reaction is carried out at 40° C., wherein the dinitrile compound is represented by Formula 1:

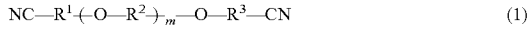

$$NC-R^1-(-O-R^2-)_m-O-R^3-CN \quad (1)$$

wherein $R^1$, $R^2$ and $R^3$ are each independently $C_1$-$C_5$ alkylene or alkenylene and m is an integer from 1 to 5.

2. The method according to claim 1, wherein the potassium alkoxide is selected from the group consisting of potassium tert-butoxide, potassium tert-pentoxide, and mixtures thereof.

3. The method according to claim 1, wherein the potassium alkoxide is used in an amount of 0.01 to 5 parts by weight, based on 100 parts by weight of the alcohol compound.

4. The method according to claim 1, wherein the alcohol compound is selected from the group consisting of ethylene glycol, propylene glycol, butylene glycol, pentylene glycol, and mixtures thereof.

5. The method according to claim 1, wherein the nitrile compound having a terminal carbon-carbon unsaturated bond is selected from the group consisting of acrylonitrile, 3-butenenitrile, 4-pentenenitrile, and mixtures thereof.

6. The method according to claim 1, wherein the dinitrile compound is selected from the group consisting of 3,5-dioxaheptanedinitrile, 1,4-bis(cyanoethoxy)butane, bis(2-cyanoethyl)-monoformal, bis(2-cyanoethyl)-diformal, bis(2-cyanoethyl)-triformal, ethylene glycol bis(2-cyanoethyl)ether, bis(2-(2-cyanoethoxy)ethyl)ether, 4,7,10,13-tetraoxahexadecanedinitrile, 4,7,10,13,16-pentaoxanonadecane-1,14-dinitrile, 3,6,9,12,15,18-hexaoxaeicosan dinitrile, 4,10-dioxa-undecanedinitrile, 1,10-dicyano-3,8-dioxadecane, 4,10-dioxa-tridecanedinitrile, 6,9-dioxa-tetradecanedinitrile, and mixtures thereof.

7. The method according to claim 1, wherein the nitrile compound having a terminal carbon-carbon unsaturated bond is acrylonitrile.

* * * * *